US00PP13514P2

(12) United States Plant Patent
Carruth

(10) Patent No.: US PP13,514 P2
(45) Date of Patent: Jan. 28, 2003

(54) MINIATURE ROSE PLANT NAMED 'WEKSNACARE'

(75) Inventor: Thomas F. Carruth, Altadena, CA (US)

(73) Assignee: Weeks Wholesale Rose Grower Inc., Upland, CA (US)

( * ) Notice: Subject to any disclaimer, the term of this patent is extended or adjusted under 35 U.S.C. 154(b) by 0 days.

(21) Appl. No.: 09/995,070

(22) Filed: Nov. 27, 2001

(51) Int. Cl.[7] ..... A01H 5/00
(52) U.S. Cl. ..... Plt./122
(58) Field of Search ..... Plt./122

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Miniature rose suitable for garden decoration, having flowers of velvet red coloration with a white eye.

1 Drawing Sheet

BOTANICAL CLASSIFICATION

*Rosa hybrida.*

VARIETY DENOMINATION

WEKSNACARE.

BACKGROUND OF THE INVENTION

This invention relates to a new and distinct variety of Miniature Rose. The varietal denomination of the new variety is 'WEKsnacare'. It has as its seed parent the variety known as 'POUlclaus' (U.S. Plant Pat. No. 9,063) and as its pollen parent the variety known as 'Times Square' (not patented).

SUMMARY OF THE INVENTION

Among the features which distinguish the new variety from other presently available and commercial rose cultivars known to the inventor are the following combination of characteristics: its flowers of velvet red coloration with a white eye, its almost thornless branches and its petal edges moderately reflexed inward at the partially open stage. The new variety has a bushy compact and rounded growing habit, suitable for outdoor garden decoration.

Asexual reporduction of the new variety by budding as performed in Kern County and Upland, Calif., shows that the foregoing and other distinguishing characteristics come true to form and are established and transmitted through succeeding asexual propagations. 'WEKsnacare' may be asexually propagated by cuttings, budding and grafting.

COMPARISON WITH PARENTS

The new variety may be distinguished from its seed parent, 'POUlclaus' by the following combination of characteristics: whereas 'POULclaus' bears semi-double deep red flowers (about 14 to about 18 petals), 'WEKsnacare' bears flowers of velvet red coloration with a white eye with significantly higher petalage (about 20 to 25 petals). The new variety has a bushy compact and rounded growing habit with short to medium length stems (about 8 to about 42 cm.) whereas the seed parent has a significantly more spreading growing habit with medium to long length stems.

The new variety may be distinguished from its pollen parent, 'Times Square' by the following combination of characteristics: whereas 'WEKsnacare' bears small size flowers in clusters of 2 to 4 per stem, 'Times Square' bears significantly larger flowers in clusters with a significantly higher number of flowers. The new variety is classified as a miniature with small size foliage whereas 'Times square' is classified as a floribunda with significantly larger foliage.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of September. Phenotypic expression may vary with environmental, cultural and climatic conditions, as well as differences in conditions of light and soil.

FLOWER

The new variety sometimes bears its flowers singly, sometimes in clusters of three to four per stem. Flowers may be borne in regular rounded to somewhat pyramidal clusters on strong short to medium stems (about 8 to about 35 cm.). Outdoors, the plant blooms abundantly and nearly continuously during the growing season. The flowers have a slight apple fragrance.

BUD

The peduncle is about 1.1 to about 2.7 cm. in length, of average caliper (about 0.1 to about 0.25 cm. in diameter), and usually erect. It is moderately smooth with many stipitate glands. Peduncle color is between 144A and 138B sometimes moderately suffused, especially on the side exposed to the sun, with between 187B and 183B.

Before the calyx breaks, the bud is about 0.6 to about 1.0 cm. in diameter at the widest point, about 1.0 to about 1.6 cm. in length, and very pointed to somewhat ovoid in shape. The surface of the bud bears some foliaceous appendages and some stipitate glands, usually with slender slightly cut foliaceous parts extending beyond the tip of the bud about ¼ or more of its length. Bud color is between 144A and 138B sometimes heavily suffused, especially on the side exposed to the sun, with between 187B and 183B.

The sepals are about 1.4 to about 2.1 cm. in length and about 0.4 to about 0.6 cm. in width at the widest point. The outer surface color of the sepal is between 144A and 138B sometimes lightly suffused, especially on the side exposed to the sun, with between 187B and 183B. The inner surface color of the sepal is between 148C and 138C and covered with fine wooly tomentum; sepal margins are lined with some stipitate glands and hairs.

As the petals open (after the calyx breaks), the bud is about 1.0 to about 1.4 cm. in diameter at the widest point, about 1.4 to about 1.9 cm. in length, and pointed to somewhat ovoid in form. The color of the under surfaces of the newly opened petals is between 70C and 56A sometime blushed on areas exposed to the sun with as dark as between 53A and 60A. At the point where the petal attaches, there is a moderately large zone of between 2D and 3D. The color of the upper surfaces of the newly opened petals is between 59A and 53A. At the point where the petal attaches, there is a moderately large zone of between 2D and 3D.

BLOOM

When fully open, the bloom ranges from about 4.1 to about 4.8 cm. in diameter. Petalage is semi-double with about 18 to 25 petals and about 4 to 8 petaloids irregularly arranged. When partially open, the bloom form is very cupped, and the petals are loosely spiraled to cupped with petal edges slightly reflexed outward. When fully open, the bloom form is cupped to somewhat flat, and the petals are more loosely cupped to undulated with petal edges slightly reflexed outward.

PETALS

The substance of the petals is moderately heavy and of medium to thick thickness, with upper surfaces moderately velvety and under surfaces slightly shiny to somewhat matte. The outer petals are broadly obovate in shape with rounded apices. The inner petals are moderately obovate to broadly oblanceolate in shape with rounded apices. The petals are about 1.5 to about 2.2 cm. in length and about 0.7 to about 1.9 cm. in width at the widest point. Petal margins are entire.

NEWLY OPENED FLOWER

The under surface color of the outer, intermediate and inner petals is between 65B and 56B. At the point where the petal attaches, there is a moderately large zone of near 4D. The upper surface color of the outer, intermediate and inner petals is between 60A and 53A. At the point where the petal attaches, there is a moderately large zone of near 4D.

The general tonality of the newly opened flower is between 60A and 53A.

THREE-DAY-OLD FLOWER

The under surface color of the outer and inner petals is between 65C and 56C. At the point where the petal attaches, there is a moderately large zone of between 155B and 4D. The upper surface color of the outer and inner petals is between 60B and 53B. At the point where the petal attaches, there is a moderately large zone of between 155B and 4D.

The general tonality of the three-day-old flower is between 60B and 53B.

On the spent bloom, the petals usually drop off cleanly.

In September in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average in number (average about 51) and are arranged regularly about the pistils; a few are mixed with petaloids. The filaments are of medium length (about 0.3 to about 0.6 cm.), most with anthers. Filaments are between 8A and 5C in color. The anthers are somewhat small to medium for the class and all open approximately at the same time. Anther color is between 21B and 23B when immature and between 164A and 164C at maturity. Pollen is abundant.

FEMALE REPRODUCTIVE ORGANS

Pistils vary in number (average about 33). The styles are moderately even, average in length (about 0.3 to about 0.6 cm.), somewhat thin to average in caliper, and moderately columnar to bunched. Stigma color is near 11B. Style color is near 1B and sometimes lightly suffused near the top with near 53B. Ovaries are usually all enclosed in the calyx.

Hips are of somewhat short to average in length (about 1.0 to about 1.5 cm.), almost rounded to somewhat globular in form, and near 25B in color when ripe. The hip surface is very smooth with moderately thick fleshy walls. The sepals are usually fugacious.

The seeds are irregularly rounded, smooth in texture, approximately 2 to about 5 per hip, about 0.2 to about 0.4 cm. in diameter at the widest point and dear 163D in color.

FOLIAGE

The compound leaves are usually comprised of three to five or more leaflets and are borne abundantly. The five-leaflet leaves are about 3.8 to about 6.9 cm. in length and about 2.5 to about 5.0 cm. in width at the widest point, moderately heavy to somewhat crisp in texture, and matte to somewhat semi-glossy in finish. The terminal leaflets are about 1.9 to about 3.0 cm. in length and 1.1 to about 2.1 cm. in width at the widest point, shaped oval to somewhat ovate with acute apices and rounded to somewhat acute bases. Their margins are usually simply serrate.

The upper surface color of the mature leaf is between 147A and 137B. The under surface color of the mature leaf is between 147B and 138B. The upper surface color of the young leaf is between 146B and 138A, sometimes moderately suffused with between 187B and 183B. The under surface color of the young leaf is between 147C and 138B, sometimes heavily suffused with between 187B and 183B.

The rachis is somewhat light to average in caliper and moderately smooth. The upper side is moderately grooved with some hairs and few stipitate glands on the edges of the grooves. The under side of the rachis is moderately smooth with many hairs and sometimes with a few small prickles. The rachis color is between 146B and 138B.

The stipules are about 0.6 to about 1.2 cm. in length and of somewhat narrow width (about 0.2 to about 0.4 cm.) with medium length straight points that usually turn out at an angle of less than 45 degrees and sometimes slightly recurve toward the stem. The stipules color is between 146B and 138B.

The petiole is about 0.4 to about 1.2 cm. in length and about 0.1 to about 0.2 cm in diameter at the widest point. The petiole color is between 146B and 138B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a bushy, compact and rounded low to medium height growth habit (about 35 to about 48 cm. in height and about 45 to about 53 cm. spread at the widest point), with very full branching. It displays moderately vigorous growth and the canes are of somewhat light to medium caliper for the class.

The color of the major stems is between 146B and 144A. They bear few large prickles that are about 0.3 to about 0.6 cm. in length. The large prickles are angled moderately downward with a somewhat short length moderately broad oval base; prickle color is between 165B and 166B. The major stem bears no small prickles.

The color of the branches is between 144A and 138B. They bear few large prickles which are of similar size and shape to the large prickles on the major stems; prickle color is between 160B and 162C. The branches bear few small prickles of similar shape and coloration.

The color of the new shoots is between 144A and 138B sometimes moderately suffused with between 187B and 183B. They bear few large prickles which are of similar size and shape to the large prickles on the major stems; prickle color is between 150C and 145C usually moderately suffused with between 187B and 183B. The shoots bear many small prickles of similar shape and coloration.

I claim:

1. A new and distinct Miniature rose plant of the variety substantially as described and illustrated herein.

* * * * *

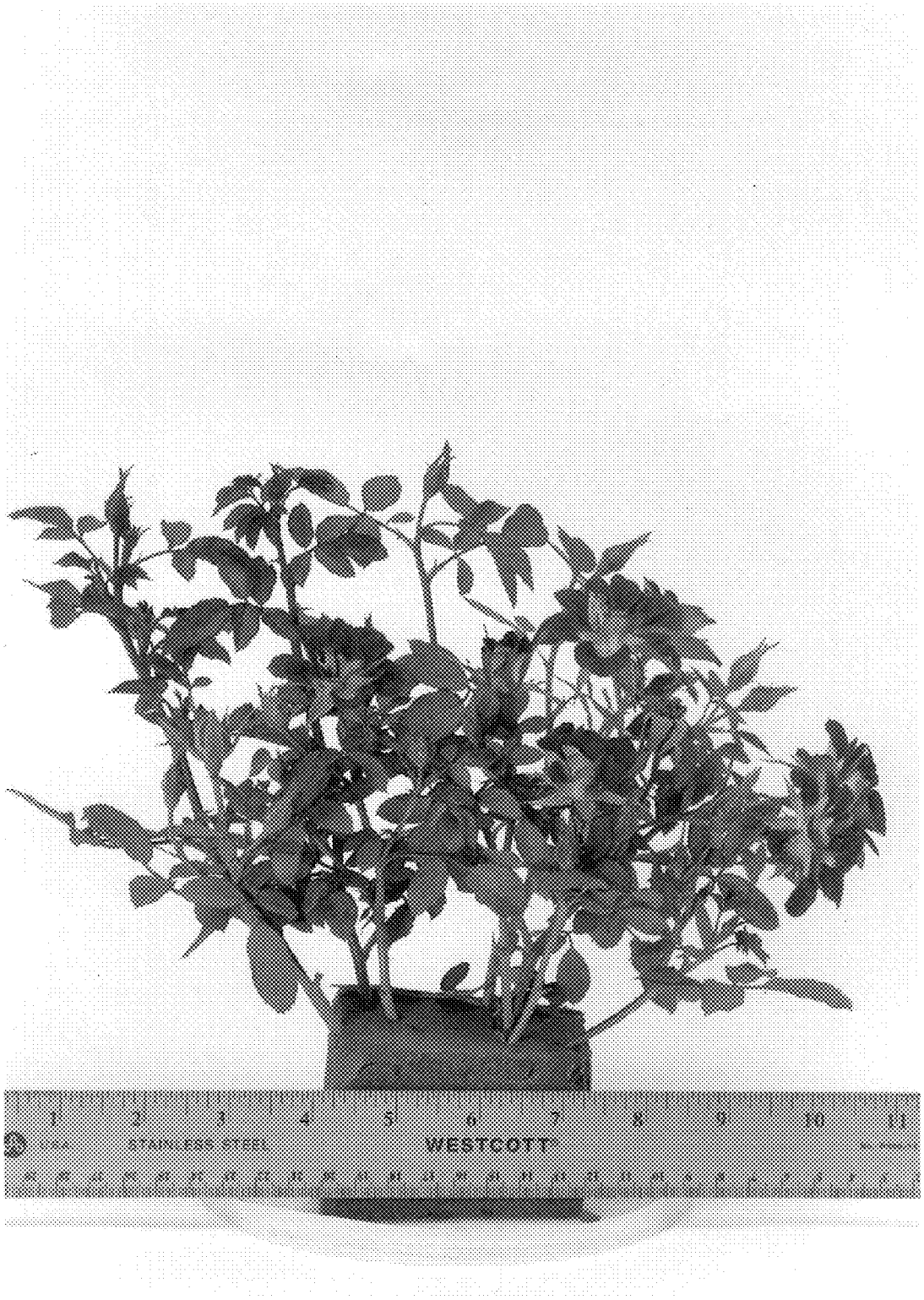
STAINLESS STEEL
WESTCOTT